United States Patent [19]

Arthur, Jr. et al.

[11] 3,963,570

[45] June 15, 1976

[54] ULTRAVIOLET-INITIATED PREPARATION OF N,N-DIBUTYL-9(10)-DIBUTYLPHOSPHONOOCTADECANAMIDE

[75] Inventors: Jett C. Arthur, Jr., Metairie; Robert R. Mod, New Orleans; James A. Harris, Pearl River, all of La.

[73] Assignee: The United States of America as represented by the Secretary of Agriculture, Washington, D.C.

[22] Filed: Sept. 26, 1974

[21] Appl. No.: 509,584

[52] U.S. Cl............................................ 204/158 R
[51] Int. Cl.²......................................... B01J 1/10
[58] Field of Search ............................. 204/158 R

[56] References Cited
UNITED STATES PATENTS 2,724,718   11/1955   Stiles et al...................... 204/158 R

OTHER PUBLICATIONS

Sasin et al., Journal of American Chemical Society, vol. 81, (1959), pp. 6275–6277.

*Primary Examiner*—Howard S. Williams
*Attorney, Agent, or Firm*—M. Howard Silverstein; Max D. Hensley

[57] ABSTRACT

N,N-Dibutyloleamide mixed with a slight excess of dibutyl phosphite and exposed to ultraviolet radiation reacts to yield N,N-dibutyl-9(10)-dibutylphosphonooctadecanamide, which is useful in imparting antimicrobial activity to cellulosic textiles and other articles.

5 Claims, No Drawings

ULTRAVIOLET-INITIATED PREPARATION OF N,N-DIBUTYL-9(10)-DIBUTYLPHOSPHONOOCTADECANAMIDE

This invention relates to a process for the preparation of phosphorus-containing organic compounds with antimicrobial activity. More particularly this invention relates to a process for the preparation of N,N-dibutyl-9(10)-dibutylphosphonooctadecanamide from the reaction of N,N-dibutyloleamide with dibutylphosphite. The mixture is photolyzed to initiate reaction of the internal double bonds and obtain addition of the compounds.

The object of this invention is to provide a process for the preparation of N,N-dibutyl-9(10)-dibutylphosphonooctadecanamide employing ultraviolet radiation to initiate the reaction.

EQUATIONS PERTINENT TO REACTIONS OF THIS INVENTION:

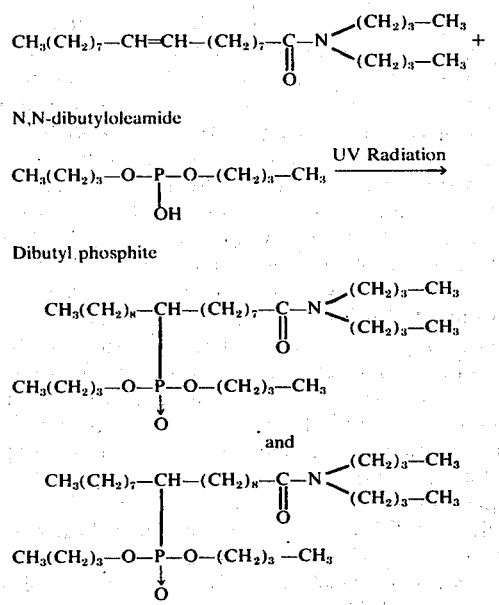

Note: Theoretically the reaction yields two forms of the product, currently identifiable as N,N-Dibutyl-9(10)-dibutylphosphonooctanamide.

PRIOR ART AND BACKGROUND OF THE INVENTION

The free radical addition of dibutyl phosphites to terminal and internal double bonds of monounsaturated amides initiated by exposure to gamma-radiation from cobalt-60 was obtained in high yields. (See "Free Radical Addition of Dialkyl Phosphites to N,N-Disubstituted Amides of Unsaturated Fatty Acids and Screening of the Products for Antimicrobial Activity" by R. R. Mod et al., which appears in the Journal of the American Oil Chemists' Society, Vol. 49, pp. 634–635 (1972) and "Phosphonated N,N-Disubstituted Fatty Amides" by R. R. Mod et al., U.S. Patent Application Ser. No. 335,860, Feb. 26, 1973 3,911,120.) now U.S. Pat. No. 3,911,120. Addition of dialkyl phosphites to unsaturated compounds containing terminal and isolated double bonds that was initiated in the presence of peroxides or ultraviolet radiation has been reported. (See "The Preparation of Dialkyl Alkylphosphonates by Addition of Dialkyl Phosphites to Olefins," by A. R. Stiles et al., which appears in the Journal of the American Chemical Society, Vol. 80, pp. 714–716 (1958); "Phosphorus Derivatives of Fatty Acids. VII. Addition of Dialkyl Phosphonates to Unsaturated Compounds," by R. Sasin, et al., which appears in the Journal of the American Chemical Society, Vol. 81, pp. 6275–6277 (1959); "Evaluation of Dialkyl 11-Phosphonoundecanoates and P,P-Dialkyl 9(10)-Phosphonostearates as Plasticizers for Vinyl Chloride Polymers," by D. W. Swern, et al., which appears in the Journal of Chemical and Engineering Data, Vol. 5, pp. 484–485 (1960)).

Attempts to initiate the reaction of dialkyl phosphites with alkyl oleates by exposure to ultraviolet radiation from a high-pressure quartz-mercury-arc lamp were unsuccessful, and the reactants were recovered unchanged. (See "Phosphorus Derivatives of Fatty Acids. VII. Addition of Dialky Phosphonates to Unsaturated Compounds," by R. Sasin, et al., which appears in the Journal of the American Chemical Society, Vol. 81, pp. 6275–6277 (1959)). This suggested that initiation of reactions of the internal double bonds of these systems by exposure to ultraviolet radiation was unlikely.

SUMMARY OF THE INVENTION

Now we have found that by the process of this invention reaction of internal double bonds in certain organic systems can be initiated by exposure to ultraviolet radiation using selected wavelengths and that reactions of internal double bonds which are initiated by the use of ultraviolet light, contrary to the findings reported in the prior art, can give products in high yields.

PREFERRED EMBODIMENTS OF THE PRESENT INVENTION

The instant invention defines a new, facile process for the preparation of N,N-dibutylphosphonooctadecanamide comprising: (1) mixing N,N-dibutyloleamide with an excess of dibutyl phosphite, typically in the ratio of one mole to three moles, respectively; (2) placing about 10 grams of this mixture in a quartz tube; (3) exposing this mixture to ultraviolet radiation (16 lamps with maximum wavelength intensities at 2537, 3000, or 3500 angstroms or 8 lamps with maximum wavelength intensities at 2537 angstroms plus 8 lamps with maximum wavelength intensities at 3500 angstroms) for about 5 to 17 hours; (4) dissolving the products in Skelly B solvent; (5) passing this solution through a column of activated alumina and stripping; and (6) giving a product in about 70 to 90 percent yields.

The extent of ultraviolet initiation of the reactions of the internal double bonds of N,N-dibutyloleamide and dibutyl phosphite was greatest in the ultraviolet radiation systems that utilized lamps with maximum wavelengths of 2537 angstroms. The maximum absorption of ultraviolet radiation by dibutyl phosphite was at about 2200 angstroms; the maximum absorption of ultraviolet radiation by N,N-butyloleamide was at about 2700 angstroms. The lamps which emitted ultraviolet radiation with a maximum wavelength intensities at 2537 angstroms also had side bands with wavelengths of 2200 angstroms and 2700 angstroms. Also, the container in which the mixture was irradiated was quartz that would allow ultraviolet radiation with these wavelengths to be absorbed by the reactants, thereby depositing energy within the reactants in sufficient amount to initiate the reactions of the internal double bonds of the reactants. By the process of this invention the absorption and deposition of sufficient ultraviolet radiation energy within the reactants was allowed, and the reactions of the internal double bonds were initiated by ultraviolet radiation without the addition of contaminating transfer agents, such as peroxides, as reported by investigators in the prior art.

Reiterating, the product of this invention was produced by mixing 10 grams of N,N-dibutyloleamide and a quantity of dibutyl phosphite which would provide a ratio of 1:3 moles, respectively, then the mixture was exposed to ultraviolet radiation, using 8 lamps with maximum wavelength intensities at 2537 angstrom units plus 8 lamps with maximum wavelength intensities at 3500 angstrom units, for a period of 12 hours to give 92% yield of the products of this invention, the two forms of N,N-dibutylphosphonooctadecanamide. Fruits of these labors, other than the products, are: (1) the infrared spectra of which established the presence of phosphonates and the absence of phosphites; (2) the nuclear magnetic resonance spectra of which showed up significant impurities in the products and confirmed the presence of phosphonate and amide groups; and (3) the elemental analyses of which were: carbon, 69.55% found, 69.46% calculated theoretical; hydrogen, 12.14% found, 12.01% calculated theoretical; nitrogen, 2.28% found, 2.38% calculated theoretical; and phosphorus, 5.17% found, 5.27% calculated theoretical.

Evaluation of the product produced by the process of this invention indicates that the N,N-dibutylphosphonooctadecaneamide thus produced had antimicrobial activity and more specifically, that the compound inhibited the growth of *Escherichia coli*.

The bioactivity of the phosphorus-containing compound prepared by the process of this invention has been established in vitro but, as will be apparent to those skilled in the art pertaining to the growth or inhibition of bacteria, yeast, and molds, the compound, besides used as such, will for utilitarian purposes commonly be formulated using a diluent that can be either liquid, gel, or solid, such as cellulosic textiles.

The following examples are provided to facilitate comprehension of the present invention and should not be construed as limiting the invention in any manner whatsoever.

EXAMPLES

In the process of investigative work which led to the process of the present invention several series of experiments were carried out and seven specific examples were selected to illustrate the preferred embodiments of the invention. The results of these seven are presented for evaluation in the table, below.

| Example No. | UV radiation Wavelength, A | No. of lamps | Time of irradiation hr. | Yield, % | Elemental analysis, % | | | |
|---|---|---|---|---|---|---|---|---|
| | | | | | C | H | N | P |
| 1 | 2537 | 16 | 17 | 91 | 70.35 | 12.23 | 2.21 | 4.94 |
| 2 | 2537 | 16 | 5.5 | -- | 73.07 | 12.43 | 2.50 | 2.52 |
| 3 | 2537 | 8 | | | | | | |
| | 3500 | 8 | 12 | 92 | 71.16 | 12.18 | 2.48 | 4.23 |
| 4 | 2537 | 8 | | | | | | |
| | 3500 | 8 | 17 | -- | 69.55 | 12.14 | 2.28 | 5.17 |
| 5 | 3000 | 16 | 17 | 71 | 74.97 | 12.29 | 2.92 | 2.15 |
| 6 | 3500 | 16 | 16 | -- | 71.62 | 12.19 | 2.42 | 3.86 |
| 7 | 3500 | 16 | 5.5 | -- | 76.16 | 12.74 | 3.08 | 1.13 |

N,N-Dibuty-9(10)-dibutylphosphonooctadecanamide was prepared by an ultraviolet irradiation process by the methods of Examples 1 through 7 wherein: (1) exposing a mixture (10 grams) of N,N-dibutyloleamide and dibutyl phosphite in the ratio of one mole to three moles, respectively, in a quartz tube by the method of Example 1 to ultraviolet radiation consisting of 16 lamps with maximum wavelength intensities at 2537 angstroms at ambient temperature, 40° to 50°C, for 17 hours; (2) dissolving the products in Skelly B solvent; (3) passing this solution through a column of activated alumina and stripping; (4) giving a product in 91 percent yield; (5) having infrared spectra establishing the presence of phosphonates and the absence of phosphites; nuclear magnetic resonance spectra showing no significant impurities in the products and confirming the presence of phosphonate and amide groups; and elemental analyses of carbon 70.35 percent, hydrogen 12.23 percent, nitrogen 2.21 percent, and phosphorus 4.94 percent.

By the method of Example 1, Examples 2 through 7 show the effects of ultraviolet radiation conditions and times of irradiation on the yields and properties of the products of N,N-dibutyl-9(10)-dibutylphosphonoctadecanamide. The infrared spectra and nuclear magnetic resonance spectra of the products produced by the methods of Examples 2 through 7 established the presence of phosphonates and the absence of phosphites and showed no significant impurities and the presence of phosphonate and amide groups, respectively. The elemental analyses of the products produced by the methods of Examples 2 through 7 confirmed the incorporation of amide and phosphonate groups in the products. The product produced by the method of Example 4 had elemental analyses almost equal to a product of N,N-dibutyl-9(10)-dibutylphosphonooctadecanamide with full incorporation of phosphonate and amide groups, as follows: carbon, 69.55% found, 69.46% calculated theoretical; hydrogen, 12.14% found, 12.01% calculated theoretical; nitrogen, 2.28% found, 2.38% calculated theoretical; and phosphorus, 5.17% found, 5.27% calculated theoretical.

We claim:
1. A process for preparing N,N-dibutyl-9(10)-dibutylphosphonooctanamide, which is represented by the general formula:

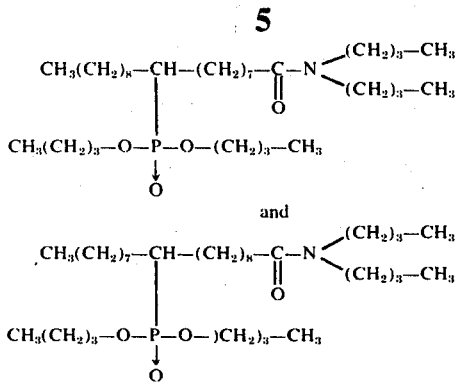

and the process comprising exposing a mixture consisting essentially of N,N-dibutyloleamide and dibutyl phosphite in about 1:3 molar ratio to wavelength intensities selected from maximum wavelength group of 2537, 3000, and 3500 angstrom units, for periods of time of about from 5.5 to 17 hours.

2. The process of claim 1 wherein the wavelength used is 2537 angstrom units.

3. The process of claim 1 wherein the wavelength used is 3000 angstrom units.

4. The process of claim 1 wherein the wavelength used is 3500 angstrom units.

5. A process for preparing N,N-dibutyl-9(10)-dibutylphosphonooctanamide, which is represented by the general formula:

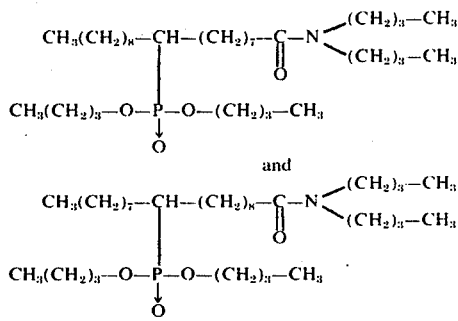

the process comprising exposing a mixture including N,N-dibutyloleamide and dibutyl phosphite in about a 1:3 molar ratio, but excluding any transfer agents, to wavelength intensities selected from maximum wavelength group of 2537, 3000 and 3500 angstrom units, for periods of time of about from 5.5 to 17 hours.

* * * * *